US006494840B1

United States Patent
Mak et al.

(10) Patent No.: US 6,494,840 B1
(45) Date of Patent: Dec. 17, 2002

(54) PORTABLE ULTRASONIC PALPATION SYSTEM

(75) Inventors: Fuk Tat Mak, Kowloon (HK); Yong Ping Zheng, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 32 days.

(21) Appl. No.: 09/629,901

(22) Filed: Jul. 31, 2000

(51) Int. Cl.$^7$ ................................................ A61B 8/00
(52) U.S. Cl. ...................... 600/446; 600/587; 600/552; 600/480; 600/443; 73/81
(58) Field of Search ................................ 600/446, 568, 600/436, 588, 300, 566, 448, 567, 159, 463, 587, 480, 552, 443; 73/81, 82

(56) References Cited

U.S. PATENT DOCUMENTS

| 4,127,114 A | * | 11/1978 | Bretscher ................. 600/480 |
| 4,771,792 A | * | 9/1988 | Seale ...................... 600/552 |
| 5,103,825 A | * | 4/1992 | Hokanson et al. ......... 600/443 |
| 5,524,636 A | * | 6/1996 | Sarvazyan et al. ........ 600/587 |
| 5,678,565 A | * | 10/1997 | Sarvazyan ................. 600/587 |
| 6,134,954 A | * | 10/2000 | Suresh et al. .............. 73/81 |

\* cited by examiner

Primary Examiner—Marvin M. Lateef
Assistant Examiner—Ruby Jain
(74) Attorney, Agent, or Firm—Leydig, Voit & Mayer, Ltd.

(57) ABSTRACT

A portable ultrasound palpation device for measuring the Young's modulus and the thickness of a soft tissue layer includes a hand-holdable palpation probe having an ultrasonic transceiver connected in series with a load cell. During a test, the probe is placed on the tissue surface with a bony substratum. As the operator manually loads and unloads the probe on the tissue surface, a program embedded in a microprocessor module continuously causes the ultrasound emitter to emit ultrasound pulses into the soft tissue. The ultrasound echo signal reflected from the bony interface is received and its flight time is used by the program to calculate the original thickness and the deformation of the soft tissue. The corresponding load applied to the tissue is continuously recorded by the load cell, its driver, and amplifier module, and the data collection module. After collecting the data for a preset number of loading-unloading cycles, the program computes the Young's modulus of the soft tissue from the load-indentation response using an analytical solution of indentation on a layer.

6 Claims, 18 Drawing Sheets

| a/h<br>ν | 0 | 0.2 | 0.4 | 0.6 | 0.8 | 1 | 1.5 | 2 |
|---|---|---|---|---|---|---|---|---|
| 0.1 | 1.000 | 1.207 | 1.459 | 1.717 | 1.997 | 2.293 | 3.107 | 3.898 |
| 0.2 | 1.000 | 1.212 | 1.479 | 1.755 | 2.055 | 2.371 | 3.222 | 4.058 |
| 0.3 | 1.000 | 1.207 | 1.472 | 1.784 | 2.124 | 2.480 | 3.400 | 4.335 |
| 0.35 | 1.000 | 1.218 | 1.502 | 1.839 | 2.211 | 2.603 | 3.629 | 4.685 |
| 0.4 | 1.000 | 1.232 | 1.542 | 1.917 | 2.337 | 2.789 | 3.996 | 5.271 |
| 0.45 | 1.000 | 1.252 | 1.599 | 2.031 | 2.532 | 3.085 | 4.638 | 6.380 |
| 0.5 | 1.000 | 1.281 | 1.683 | 2.211 | 2.855 | 3.609 | 5.970 | 9.069 |

PORTABLE ULTRASONIC PALPATION SYSTEM

BACKGROUND OF THE INVENTION

1. Field of the Invention

The present invention relates to the use of indentation and ultrasound techniques to quantitatively assess the mechanical properties of soft tissues, and in particular of a soft tissues covering a musculoskeletal system of a body.

2. Description of Prior Art

The human musculoskeletal system is entirely covered by layers of soft tissues. At the body support interfaces, such as buttock tissues interfacing with a seat, residual limb tissues interacting with a prosthetic socket, and plantar tissues of a foot interacting with an in-sole/ground, significant loads are transmitted via skin to underlying tissues. Biomechanical assessment of skin and underlying soft tissues is relevant to the designs of respective body support interfaces. These issues are relevant to many clinical rehabilitation problems, such as the design of special cushions for a spinal cord injury, special orthotics for diabetic feet, and custom prosthetic sockets for amputees. Traditionally, biomechanical properties of limb soft tissues are evaluated by palpation. Such a subjective assessment requires substantial experience acquired through trial and error. The qualitative nature makes knowledge accumulation difficult and makes teaching-learning imprecise.

Among the various biomechanical testing protocols, indentation test is an effective and relatively simple way to make biomechanical assessment of the skin and subcutaneous tissues under compression. Tests themselves very much resemble that of palpation. However, existing indentation apparatuses that have been proposed are not feasible for extensive clinical application. In most cases, indentors are driven by electromechanical or pneumatic devices. This makes testing systems difficult to handle, and difficult to operate, with potential hazards to the soft tissues. One of the latest example of electromechanical driving indentation apparatus was introduced in A. P. Pathak, et al., *A rate-controlled indentor for in vivo analysis of residual limb tissues*, IEEE Transactions on Rehabilitation Engineering; Vol. 6, 12–20 (1998). The application of this device in clinical field is still difficult due to the large dimension of the indentation device. A hand-held indentation apparatus with a laser distance sensor to monitor the indentor displacement is disclosed in M. Horikawa, et al., *Non-invasive measurement method for hardness in muscular tissues*, Medical and Biological Engineering and Computing; Vol. 31, 623–627 (1993). The measurement of the displacement by laser has the drawback that the result is significantly influenced by the misalignment, the indented area if the laser beam is too close to the indentor, and the curvature of the limb if the laser beam is too far from the indentor. Furthermore, the existing indentation apparatuses have the drawback that the deformation of the soft tissue is commonly determined by the movement of the indentor, so the soft tissue thickness can not be suitably measured in the test. The stiffness measured in this manner would reflect not only the material properties of the tissues but also some geometric factors. To extract accurate material parameter, the tissue thickness might be obtained using other approaches, such as MRI, X-ray and ultrasound techniques.

Conventional ultrasonic imaging techniques have been used to study the elastic properties of a soft tissue by measuring the strain in the tissue subjected to a given stress. An approach has been attempted to determine the tissue elasticity, by applying a low frequency vibration to the tissue surface while measuring the amplitude and phase of the internal tissue vibration using ultrasound Doppler technique. See e.g. T. A. Krouskop, et al., *A pulsed doppler ultrasonic system for making non-invasive measurement of mechanical properties of soft tissue*, J. Rehab. Res. Dev. Vol. 24, 1–8 (1987); see also R. M. Lerner, et al., "Sonoelasticity" images derived from ultrasound signals in mechanically vibrated tissues, Ultrasound in Med. & Biol. Vol. 16, No. 3, 231–239 (1990), K. J. Parker, et al., U.S. Pat. No. 5,099,848 (1992), and Y. Yamakoshi, et al., *Ultrasonic imaging of internal vibration of soft tissue under forced vibration*, IEEE Transactions on Ultrasonics, Ferroelectrics and Frequency Control, Vol. 7, No. 2, 45–53 (1990).

Another method for imaging the tissue elasticity is disclosed in J. Ophir, et al., U.S. Pat. No. 5,107,837 (1992), J. Ophir, et al., U.S. Pat. No. 5,293,870 (1994), and M. O'Donnell, et al., *Internal displacement and strain imaging using ultrasonic speckle tracking*, IEEE Transactions on Ultrasonics, Ferroelectrics and Frequency Control, Vol. 41, 314–325 (1994). This method included emitting ultrasonic waves along a path into the soft tissue and recording an echo train resulting from an ultrasonic wave pulse. Another echo train was recorded resulting from a second ultrasonic wave emitting along the path after the tissue was compressed. A selected echo segment of the echo sequence corresponded to a particular echo source within the tissue along the beam axis of the transceiver. Time shifts in the echo segment are examined using cross-correlation technique to measure compressibilities of the tissue regions. The use of MRI for detection of shear waves in soft tissue induced by a mechanical actuator attached to the surface of the tissue is described in R. Muthupillai, et al., *Magnetic resonance elastography by direct visualization of propagating acoustic strain waves*, Science, Vol. 269, 1854–1857 (1995).

The above methods using ultrasound and MRI techniques are needed to generate the elasticity imaging of soft tissues. Their significance was the detection of tissue abnormalities, such as those caused by cancer or other lesions, and their output is the local mechanical property of internal regions of a soft tissue, not the bulk property of an entire tissue layer. For those applications, the deformation of the soft tissue was generally less than 5%, which was much smaller than those of the soft tissues interacting with supporting interfaces, such as residual limb tissue, for which 30% deformation is not uncommon in many cases. Since measurement of relative change of a material property is sufficient for many imaging purposes, these methods are usually not calibrated against any absolute values of the material parameters. This is a drawback when more accurate material parameters are needed.

SUMMARY OF THE INVENTION

It is an object of the invention to overcome these drawbacks.

According to the invention there is provided a portable ultrasonic palpation device for measuring Young's modulus of a soft tissue layer comprising a hand holdable pressure applying probe having an ultrasonic transceiver for transmitting and receiving ultrasound at an outer surface of the tissue layer, an applied pressure sensor for the probe, and a programmed computer arranged to receive signals from the transceiver and from the pressure sensor and to compute the Young's modulus of the tissue layer based on applications of manually applied different pressures to the outer surface.

The probe preferably comprises a cylindrical body having a forward tip containing the ultrasonic transceiver, and a like second cylindrical body attached end-to-end to the first cylindrical and containing the pressure sensor. The cylindrical bodies are preferably approximately 10 mm in diameter.

The computer may be programmed to provide output signals corresponding to an effective depth of the tissue layer.

The computer may be programmed to compute according to the equation:

$$E = \frac{(1-v^2)}{2a\kappa(v, a/h)} \frac{P}{w} \qquad (1)$$

where E is the Young's modulus, P the applied load, w the indentation depth, h the tissue thickness, a the radius of indentor, and K a scaling factor.

BRIEF DESCRIPTION OF THE DRAWINGS

A portable ultrasonic palpation device according to the invention will now be described by way of example in which:-

DETAILED DESCRIPTION OF THE INVENTION

Figure 1:
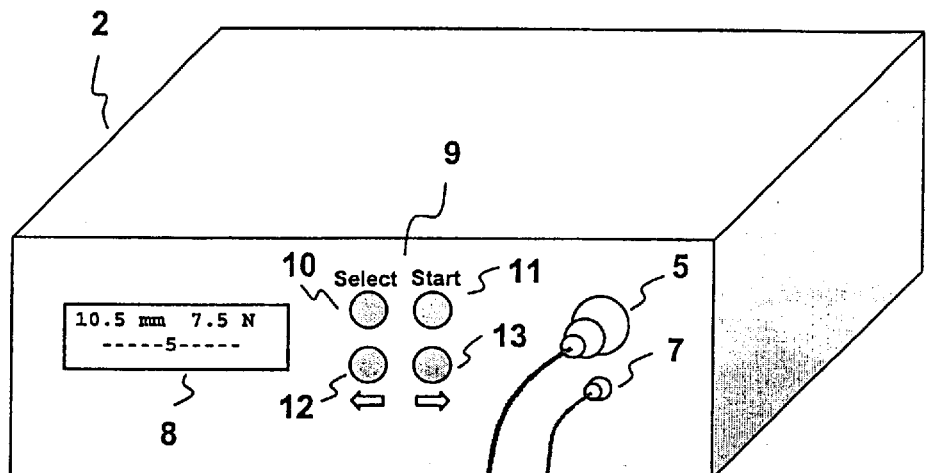
FIG. 1 illustrates the portable ultrasound palpation system

Embodiments of the invention relate to the use of indentation and ultrasound techniques to quantitatively measure the mechanical parameters of soft tissues. In the described embodiment, the device includes a finger-size probe and a portable control box. The probe comprises an ultrasound transceiver at the tip serving as the indentor and a load cell transceiver connected in series with it. A control box incorporates a microprocessor, connected to an ultrasound emitter and receiver and a load cell driver, an amplifier, data collection and timing modules and a LCD.

During use, the hand-held probe is placed on a tissue surface with a underlying bony substratum. The probe-tissue interface is lubricated with ultrasound couplant, which has ability to couple ultrasound signal from the transceiver into the soft tissue. When a controlling computer program causes the ultrasound emitter to emit an ultrasound pulse wave into the soft tissue, the ultrasound echo signal reflected from the bony interface is received and its flight time is determined by the microprocessor to compute the tissue thickness. The ultrasound speed in most soft tissues is typically around 1540 m/s. The amplitude of the reflected ultrasound echo signal is collected using the data collection module. A corresponding load applied on the tissue is recorded by via load cell. The LCD displays in real time the tissue thickness, the load applied, and a bar indicator to show a relative amplitude of the reflected ultrasound signal. Since the ultrasound reflection signal is maximal when the probe is aligned perpendicularly to the underlying bone interface, any misalignment of the probe will tend to reduce the amplitude of the reflection signal. The amplitude shown in the bar indicator helps the operator to maintain a consistent alignment of the probe.

Before cyclic tests, an original thickness of soft tissue is first measured with a manually controlled pre-load, and the maximum indentation depth and load can be preset by the operator. As the operator manually loads and unloads the probe on the tissue surface, the controlling program continuously causes the ultrasound emitter to emit ultrasound pulses into the soft tissue. The instant tissue thickness and applied load are determined and displayed. The computer provides an audio feedback using different buzzer tones to indicate whether data points exceed the preset maximum indentation depth, maximum load, pre-load, or predetermined original thickness. The operator uses these audio feedbacks to control loading and unloading sequences. After collecting the data for a preset number of loading-unloading cycles, the microprocessor module computes the Young's modulus of the soft tissue (using Equation1, see below) from the load-indentation response using an analytical solution of indentation on a layer. The Young's modulus of the soft tissue as well as the indentation rate and the original tissue thickness are displayed on the LCD after the test. Another cyclic test can follow immediately, and so on. The microprocessor calculates the mean and standard deviation of the Young's modulus, the original thickness and the indentation rate for a group of tests per uses the control of an operator.

The layer indentation model used to calculate Young's modulus is disclosed in W. C. Hayes, et al., *A mathematical analysis for indentation tests of articular cartilage*, Journal of Biomechanics; Vol. 5, 541–551 (1972) where a rigorous mathematical solution is provided. Young's modulus relating to elastic indentation of a thin elastic layer bonded to a rigid half-space with a rigid, frictionless cylindrical plane-ended indentor is given by Equation (1).

$$E = \frac{(1-v^2)}{2a\kappa(v, a/h)} \frac{P}{w} \qquad (1)$$

where E is the Young's modulus, P the applied load, w the indentation depth, h the tissue thickness, a the radius of indentor, and K a scaling factor. This scaling factor provides a theoretical correction for the finite thickness of the elastic layer, and it depends on both an aspect ratio a/h and Poisson's ratio v. The Poisson's ratio v is typically taken here to be 0.45 assuming soft tissue to be nearly an incompressible material. The radius of the indentor is known, according to the dimension of the ultrasound transceiver. The factor P/w is calculated from cyclic load-indentation responses.

The device preferably includes means to prevent influences of noise received during use of the device and changes of the alignment of the probe during a test. An auto-gain-control mean is included to maintain a consistent amplitude of ultrasound reflection signals which may differ for soft tissues of different subjects, with different tissue thickness, different underlying bony geometry, or different pathological conditions, for different probe alignment or different amount of indentation. In addition, the system includes means to select and track ultrasound echo signals reflected from the bony interface. For flexibility of operation, the device also includes means to start a measurement using a switch controllable by a hand or foot of the operator.

Referring to the drawings, in FIG. 1 the portable ultrasound palpation device has a finger-size probe 1, a control box 2, and a remote switch 3. The probe 1 is connected to the controlling box 2 via a cable 4 and a cable connector 5. The remote switch 3 is connected to the controlling box 2 via another cable 6 and cable connector 7. A LCD panel 8 (with 16×2 characters) is used to display testing parameters, results, and other information. Panel keypads 9 are used to select functions (10), adjust parameters (12, 13), and start measurements (11). During a test, the probe is held by the fingers of the operator, while the remote switch 3 is controlled by a hand or foot of the operator and used to start a test. Starting a test may also be achieved by a starting keypad 11 on the control box. Hereinafter the starting switch 3 and the starting keypad 11 are both simply referred to as the "starting key".

Figure 2:
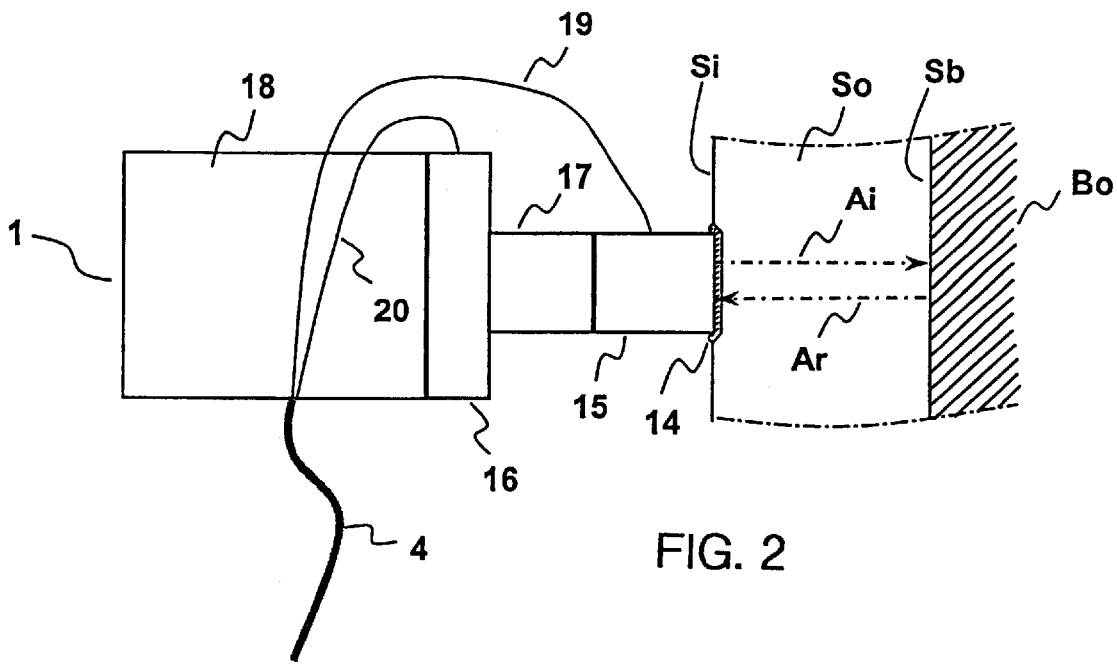
FIG. 2 illustrates a structure of a palpation probe and a propagation path of ultrasound signals.

FIG. 2 illustrates a structure of the probe and a propagation path of the ultrasound signals. In a test, the probe 1 is placed on a tissue surface Si of soft tissue So having an underlying bony substratum Bo. The probe-tissue interface is lubricated with ultrasound couplant 14. An ultrasound transceiver 15 with a diameter of 9 mm, is at the tip of the probe 1, and a compression load cell 16 is connected in series with the ultrasound transceiver 15 through a suitable connector 17. The load cell 16, comprises a resistive bridge for sensing the compression load. The other end of the load cell 16 is attached to a plastic body 18 that is held by the operator during use. There are two groups of wires, group 19 from ultrasound transceiver 15 and group 20 from load cell 16, to form the cable 4, that is enclosed by a heat shrinkable sheath, led from a side of the plastic body 18 to the control box 2 through the connector 5. Ultrasound pulses Ai are emitted from the ultrasound transceiver 15, and coupled into the soft tissue so through the ultrasound couplant 14. When the pulses encounter the bony interface Sb, an echo Ar is reflected and received by the ultrasound transceiver. The reflected signals, or echo signals are amplified and used to determine the thickness of the soft tissue So. Since the echo signals are maximal when the probe 1 is aligned perpendicularly to the bony interface Sb, any misalignment of the probe 1 will tend to reduce the amplitude of the echo signals. This characteristic may be used to help the operator to maintain a consistent alignment of the probe 1 during a test.

Figure 3:
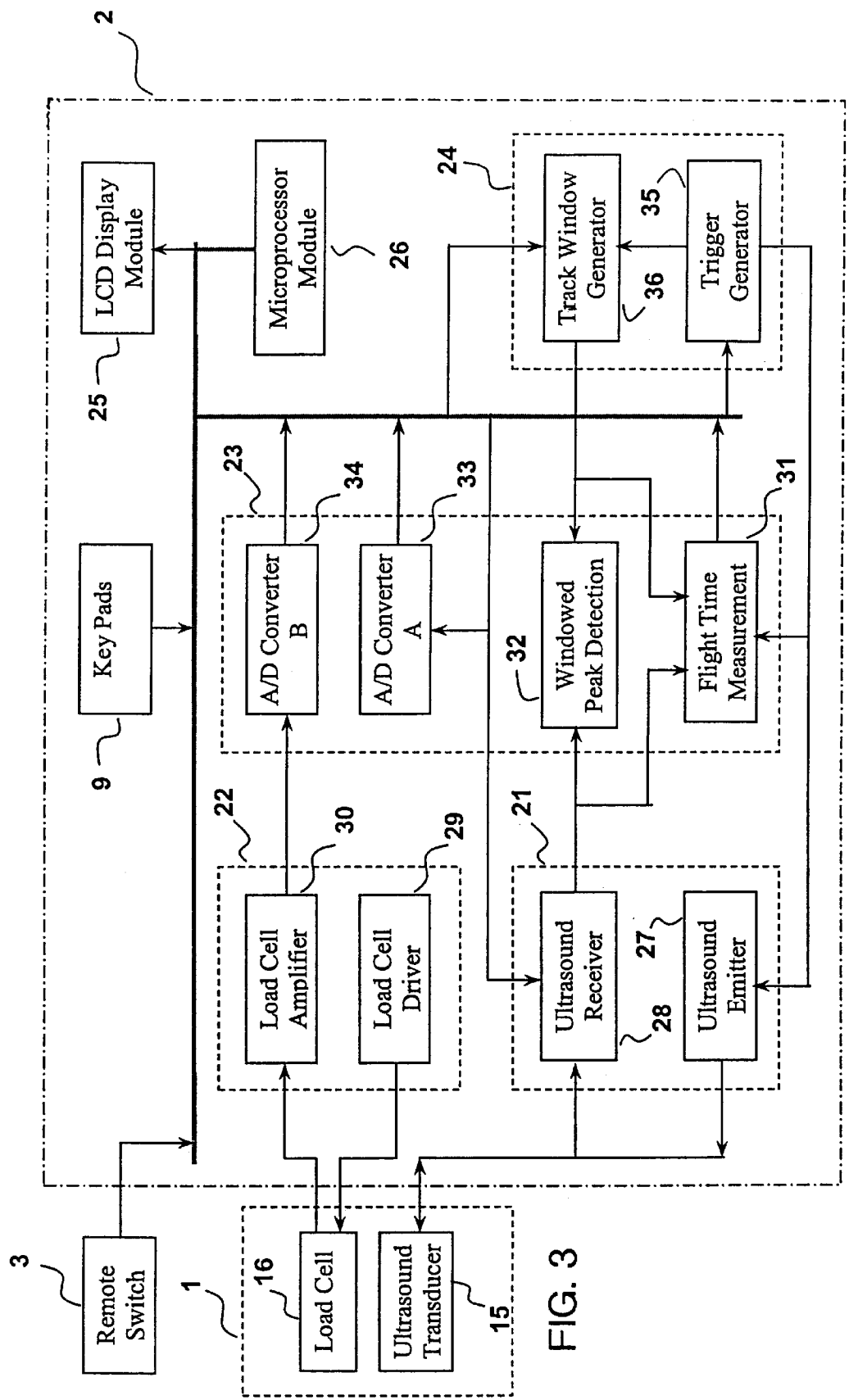
FIG. 3 is a block diagram of the portable ultrasound palpation device.

In the block diagram FIG. 3, the control box 2 includes the ultrasound emitter and receiver 21, a load cell driver and amplifier 22, a data collection module 23, a timing module 24, a LCD module 25, panel keypads 9, and a microprocessor 26. The ultrasound emitter and receiver module 21 (hereinafter simply referred to as ultrasound module) are part of an ultrasound emitting unit 27 and an ultrasound receiving unit 28. The load cell module 22 comprises a load cell driving unit 29 and a load cell amplifying unit 30. The data collection module 23 comprises a flight time measurement unit 31, a windowed peak detection unit 32, A/D converter A 33, and A/D converter B 34. The timing module 24 comprises a trigger generation unit 35 and a track window generation unit 36. The microprocessor 26 comprises a ROM and a RAM, shown in the Figure. The program is stored in the ROM, and data points collected, results generated, and other information are stored in the RAM during a measurement in a generally conventional fashion. The microprocessor 26 is connected to the other modules via data and address buses and other normal I/O ports.

Figure 4:
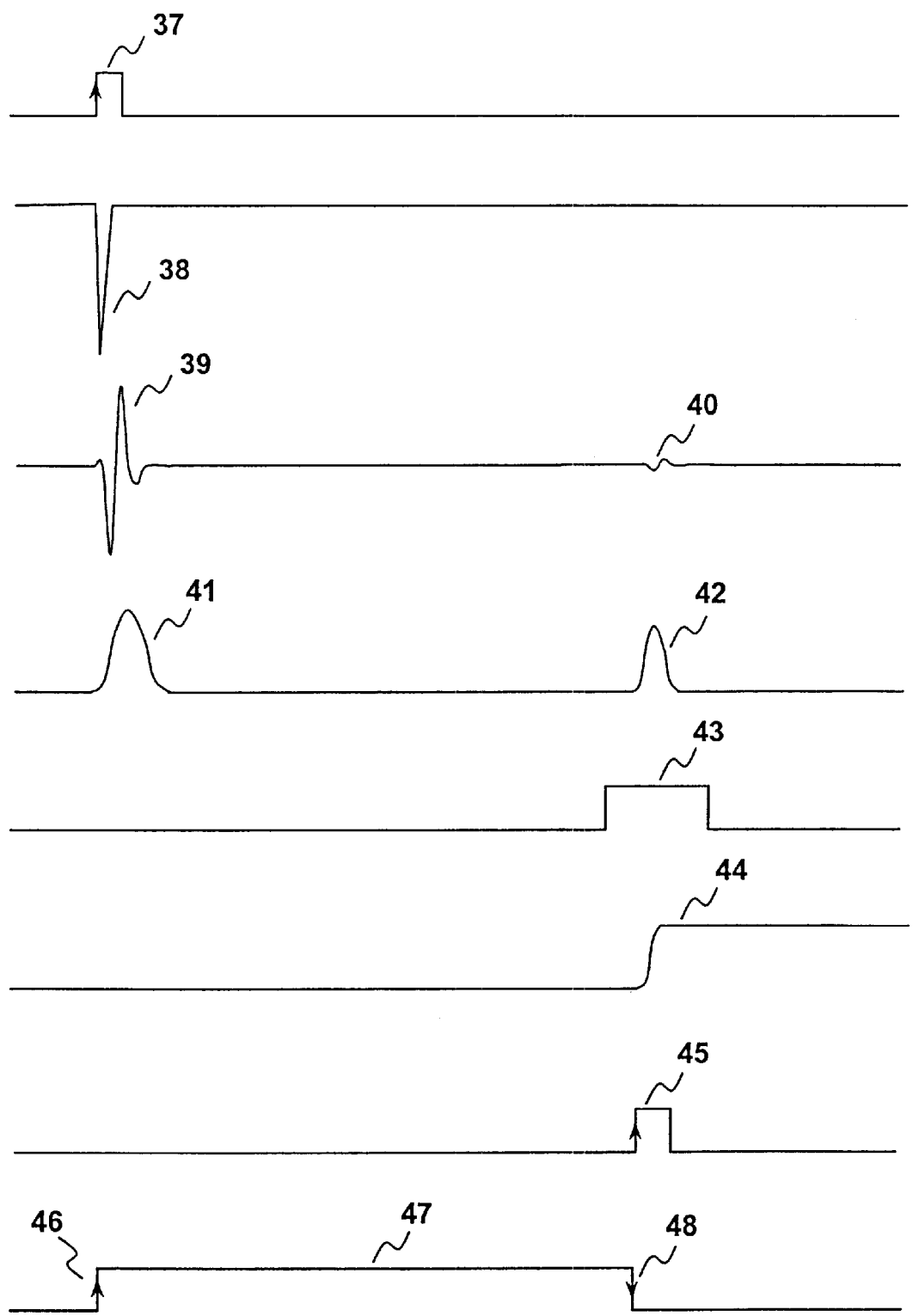
FIG. 4 is a time sequence of the different modules of a control box.

Time sequences of the different modules are shown in FIG. 4. The ultrasound emitter 27 is triggered by a trigger signal 37 generated by a trigger generation unit 35, which is stimulated by the program in the microprocessor 26. With the stimulation of the trigger signal 37, the ultrasound emitter 27 generates an electrical pulse 38 with an amplitude of 100 V, and a pulse width of 200 ns. The pulse is supplied to the ultrasound transceiver with a central frequency of 2.5 MHz, 5 MHz, or 10 MHz, via the cable 19. High frequency transceivers are normally used for thin soft tissue layers, and low frequency transceivers used for thick tissue layers. Ultrasound pulse waves 39 with corresponding frequency are then generated at the tip of the ultrasound transceiver 15, which is held against the tissue surface Si during a test. Ultrasound reflection, and echo waves 40, are received and transferred into electrical echo signal by the ultrasound transceiver 15. The ultrasound echo signals are supplied to the controlling box via cable 4 and 19 and amplified by the ultrasound receiver 28. The gain of the ultrasound receiving unit 28 is controlled by the program.

The amplified and filtered ultrasound signals 41 and 42 are led to the data collection module in two ways. In one way, the windowed peak detection unit 32 detects the amplitude of the peak of a selected echo 42 using a windowed peak holding circuit. The echo 42 is selected by a track window 43 which is generated by the track window generation unit 36. The position and the width of the track window 43 are adjustable by the program. When soft tissue is loaded and unloaded by the probe 1 during a test, the program will change the position of the window 43 back and forth to track the movement of the selected echo signal. The peak amplitude signal 44 generated by the windowed peak detection unit 32 is led to the A/D converter A 33 normally with a resolution of 8 bits. After the signal 44 is successfully digitized, the output of the peak holding circuit is reset to zero. The digitized value of the peak amplitude is then read by the program for calculation and display. During a test, if the peak amplitude of the selected echo is smaller than a preset minimum limit or larger than a preset maximum limit, the program will increase or decrease the gain of the ultrasound receiving unit accordingly to maintain a relatively stable ultrasound echo signal.

In the other way, the detected ultrasound signals 41 and 42 are led to the flight time measurement unit 31. In this unit, the signals are first amplified, then a rising edge of the selected echo is detected, and an echo position signal 45 is generated. The operation of edge detection is limited within the track window 43; a counter starts to count at the rising edge 46 of a counter enable signal 47, which is synchronized with the rising edge of the trigger signal 37, and stops counting at the falling edge 48 of the counter enable signal 47, which is synchronized with the rising edge of the echo position signal 45. The value of the counter is then read by the program. According to the value of the counter and the counting frequency, for example, 10 MHz, the flight time of the selected echo can be calculated by the program. This flight time equals double the time that it takes ultrasound signals to propagate from the tissue surface Si to the bony interface Sb if the selected echo is reflected from that interface. Using the mean speed of ultrasound in soft tissue, typically, 1540 m/s, the thickness of the soft tissue can be calculated by the program via I/O ports of the microprocessor module 26. It should be noted that there are usually more than one set of reflection echoes in practical situations. Additional echoes can arise due to reflections from intermediate interfaces of soft tissue sub-layers, such as, skin-fat interfaces, fat-muscle interfaces, muscle-muscle interfaces, or from multi-reflections of the echo between the tissue surface and the bony interface. The real tissue thickness is determined using a pretest to eliminate spurious reflections which will be described below.

The resistive bridge of the load cell 16 is driven by the load cell driving unit 29, and the load signal corresponding to the load applied on the load cell 16 is amplified by the load cell amplifying unit 30. The amplified load signal is digitized by the A/D converter B 34 with resolution of 8 bits. For each trigger signal 37, the digitized load signal is read by the program via I/O ports of the microprocessor 26.

FIGS. 10*a*–10*k* are flowcharts of the program for the operation of the device. Besides a main program, there are three subprograms PRETEST, TEST and MEASUREMENT. The function of main program is to make selection of different functions of the program and input various parameters for a test. The function of PRETEST is to determine the tissue thickness under a certain pre-load before cyclic tests. If there are multi echoes, the real tissue thickness is identified using a pretest. The function of TEST is to make a cyclic test and to extract Young's modulus. The function of MEASUREMENT is to make measurements of load and tissue thickness.

Initially, the main program first initializes the I/O ports of various modules, presets default values for various parameters, shows initializing message on the LCD (block 49), and then waits for a starting key input. If the option of changing parameters (block 50) is selected, the operator can change the number of testing cycles, the maximum limit of load and indentation depth, the status of the first cycle to be used or not, and the status of the audio feedbacks to be presented or not (block 58 through 68 in FIG. 10*b*). If there is no parameter to be changed (block 69), the program waits a starting key to be pressed to start a pretest (block 51). Before a pretest, the probe 1 is placed at the testing site with the ultrasound couplant 14 lubricating between the tissue surface Si and the tip of the probe 1, and the probe 1 is then loaded and unloaded for several times to precondition the soft tissue So. If a starting key is pressed (block 51), the subprogram PRETEST performs a pretest.

Figure 10A:
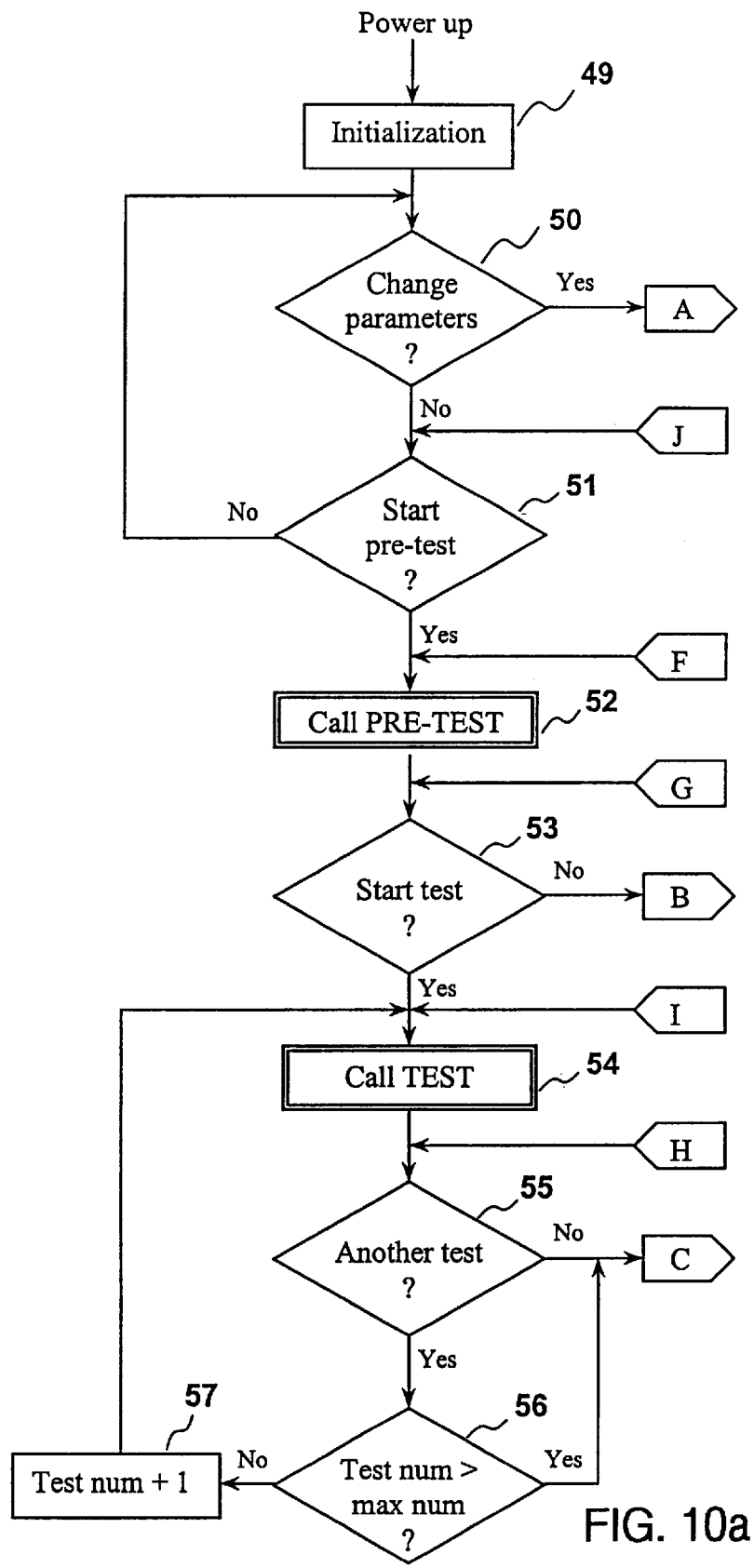
FIGS. 10a–10k are flowcharts of programs for the operation of the ultrasound palpation device.
Figure 10B:
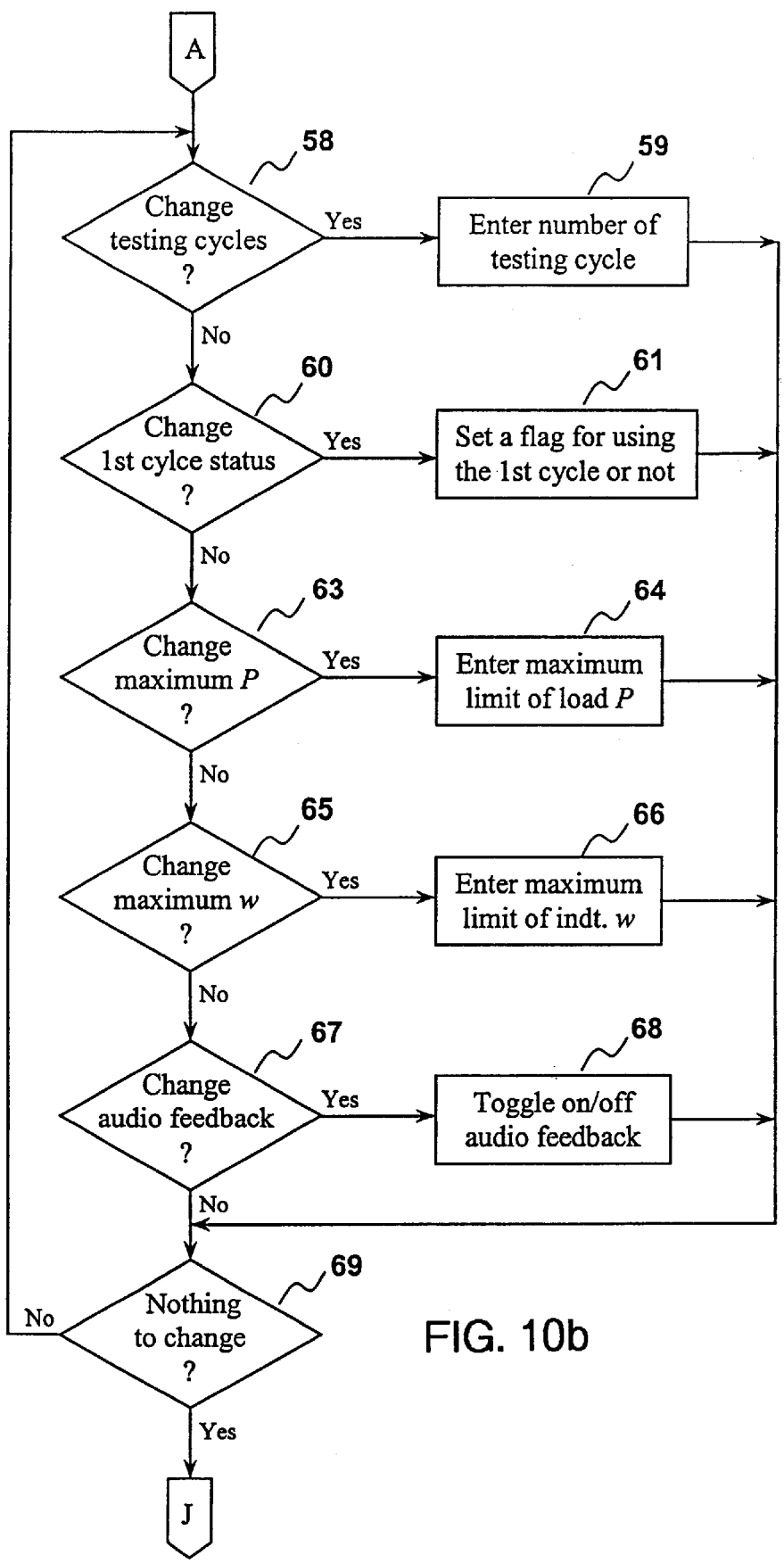
Figure 10C:
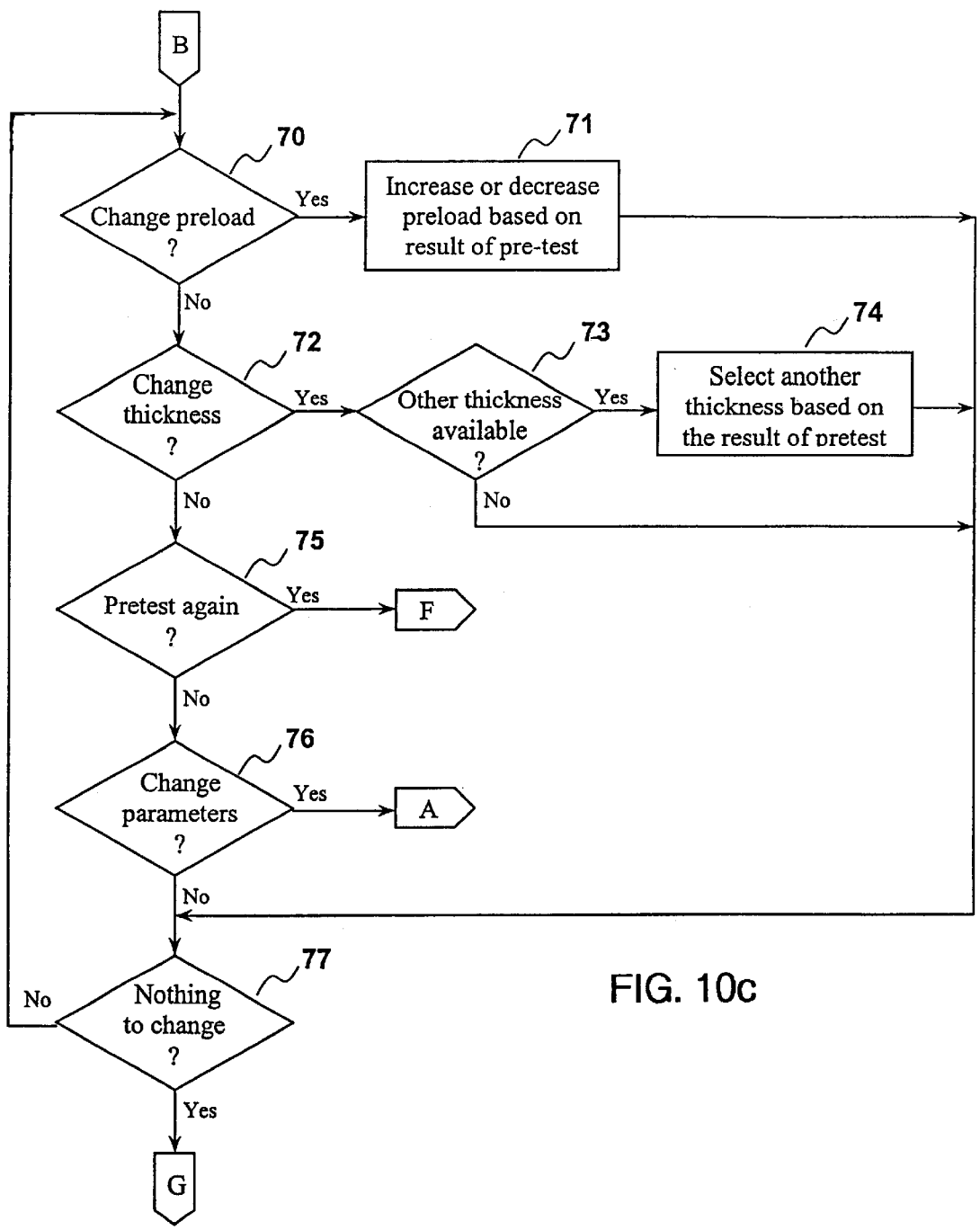
Figure 10D:
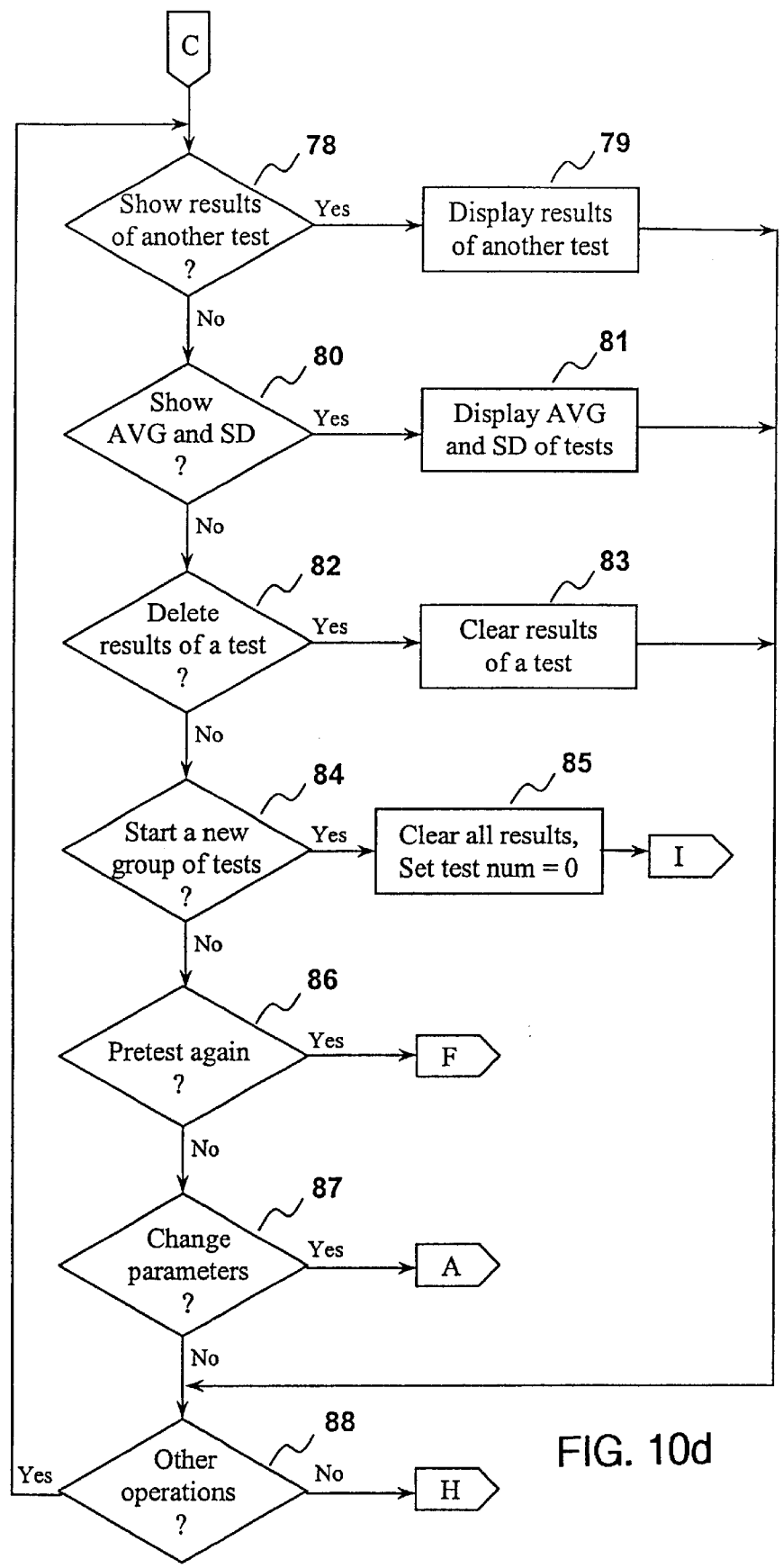
Figure 10E:
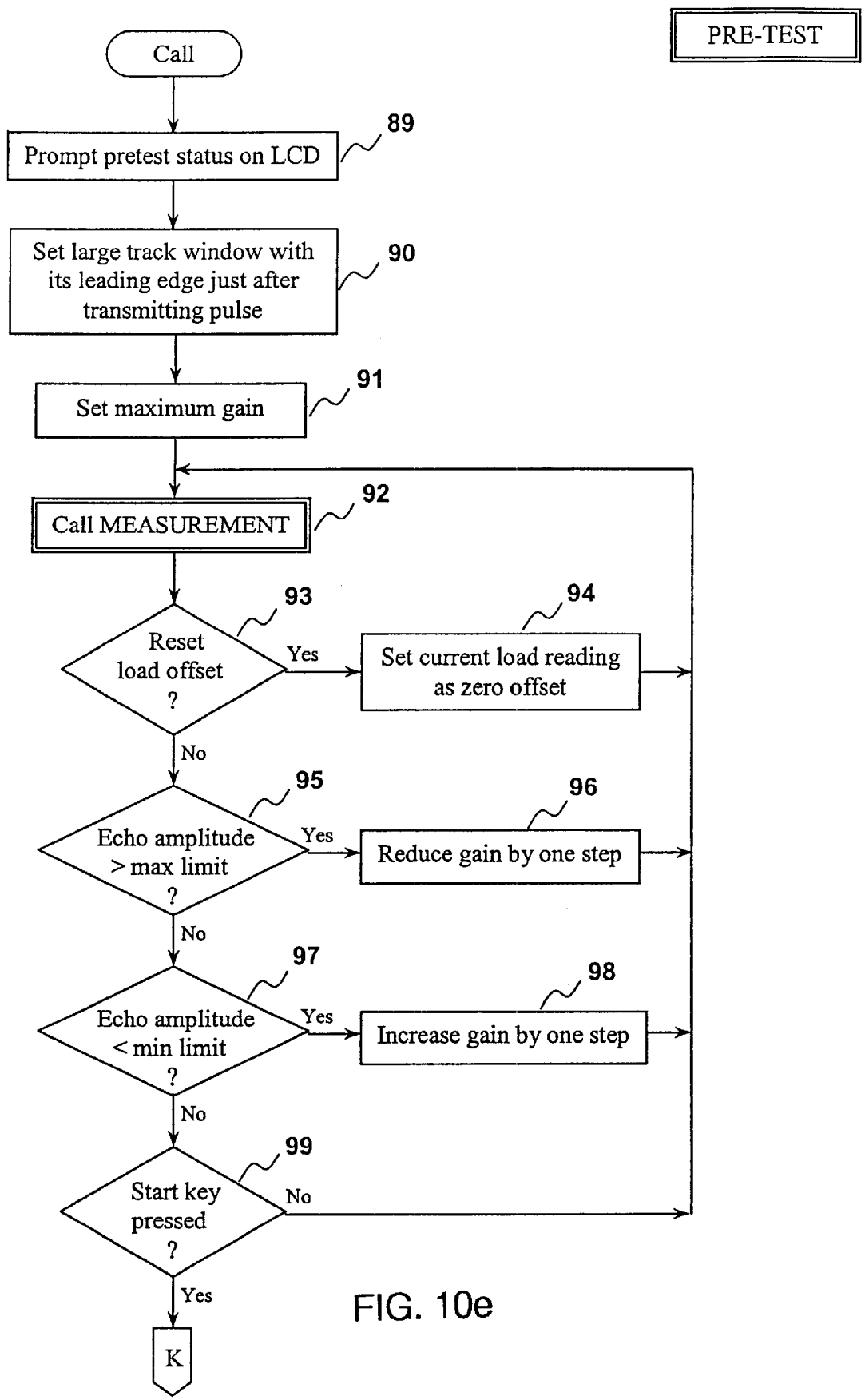
Figure 10F:
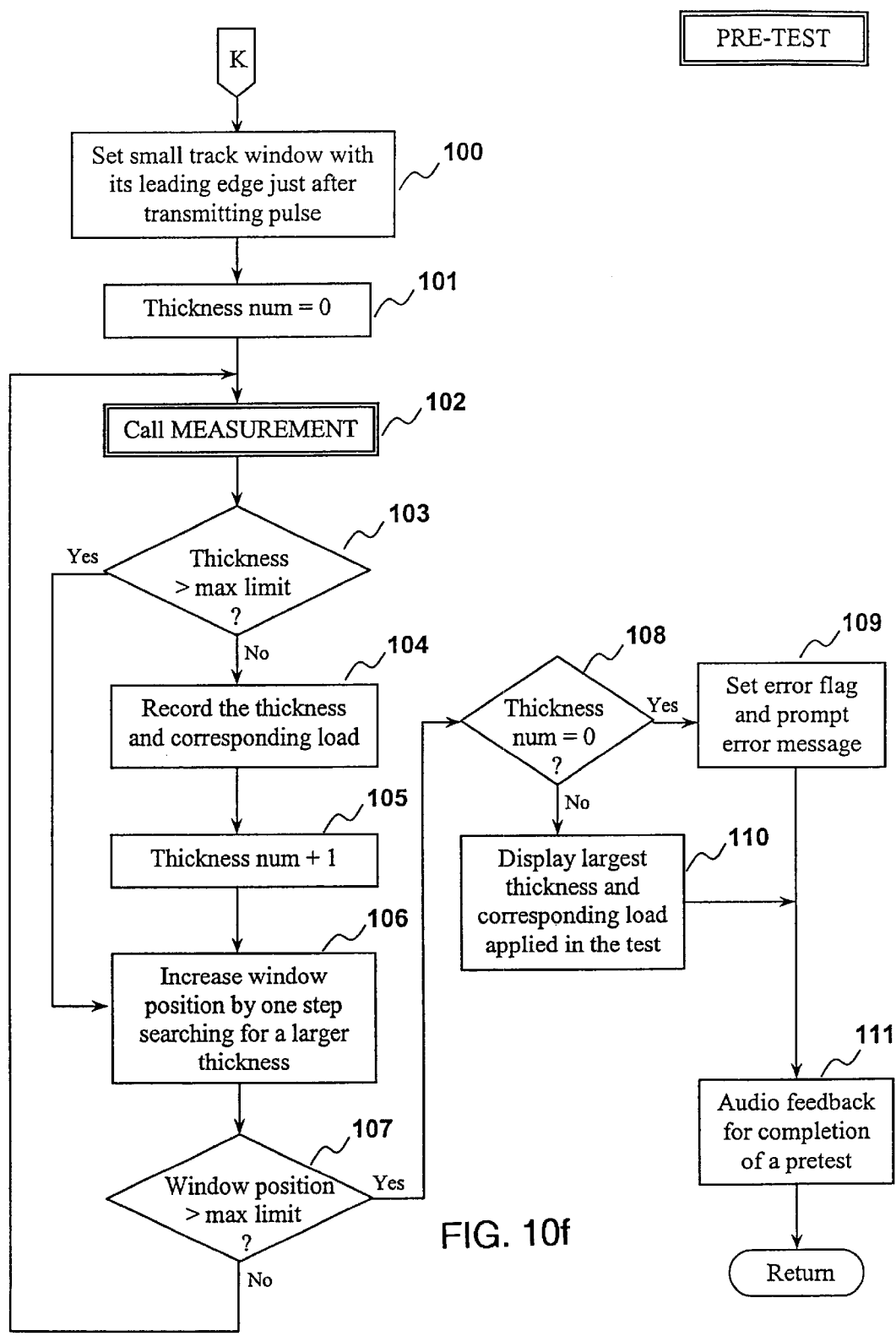
Figure 10G:
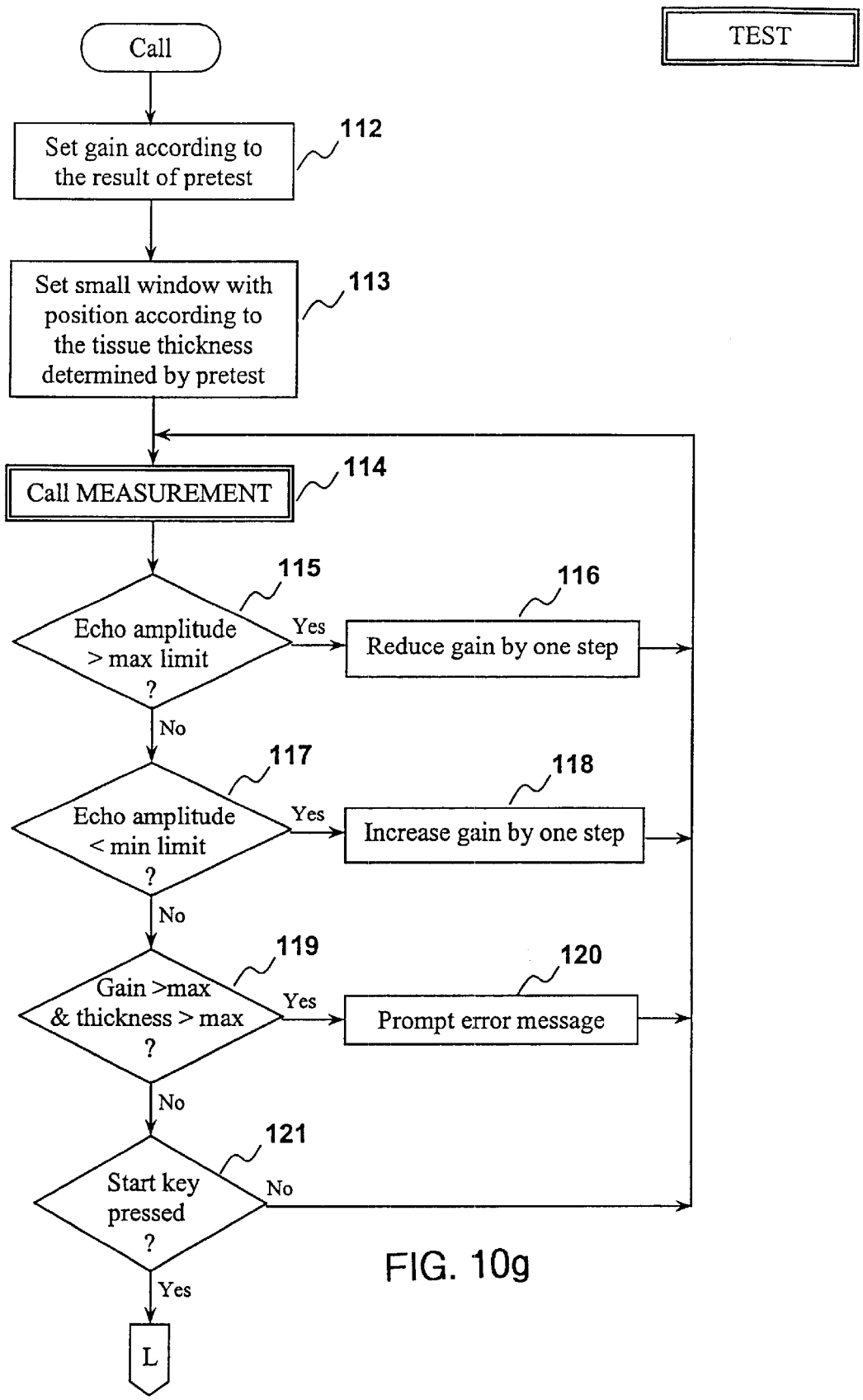
Figure 10H:
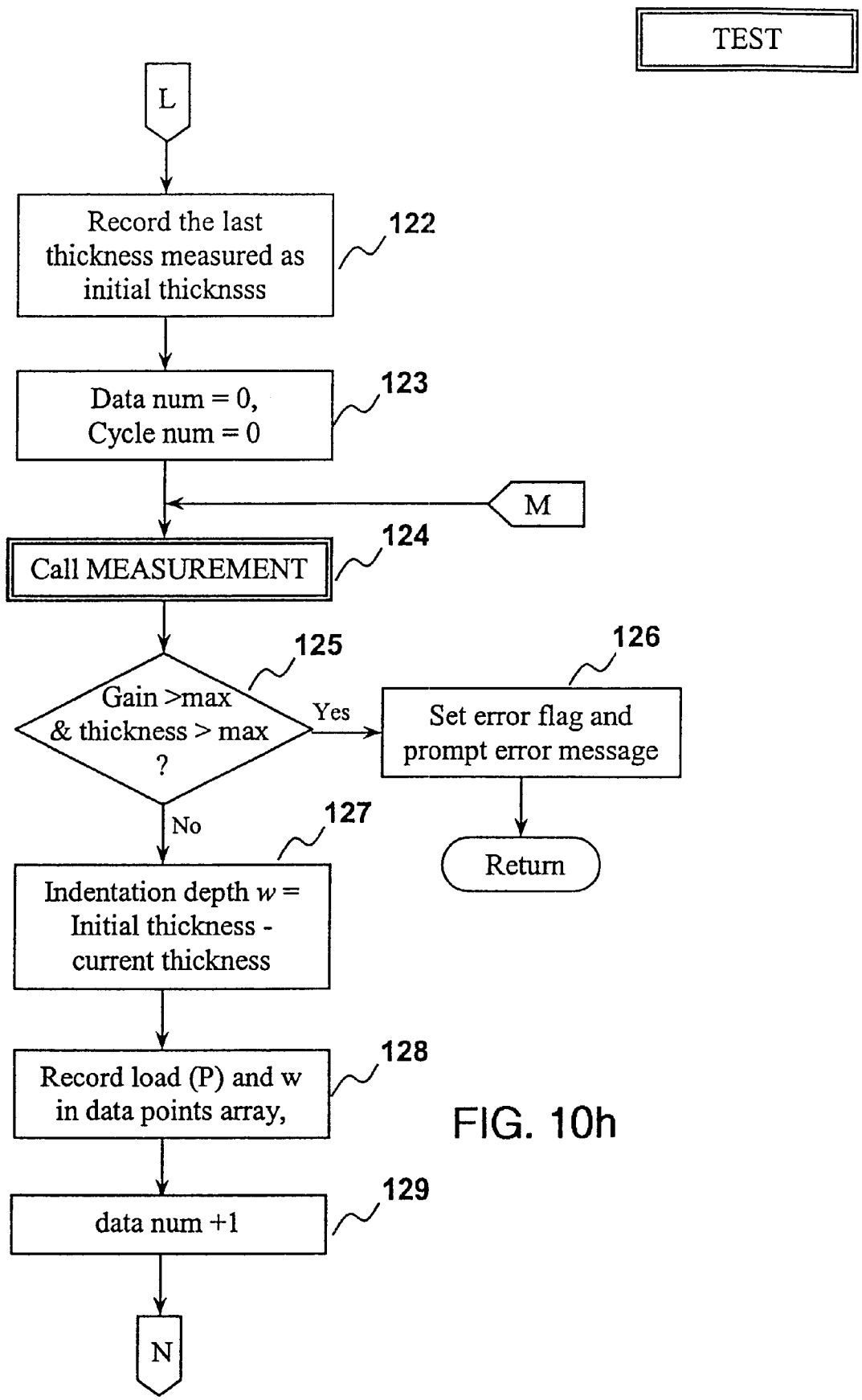
Figure 10I:
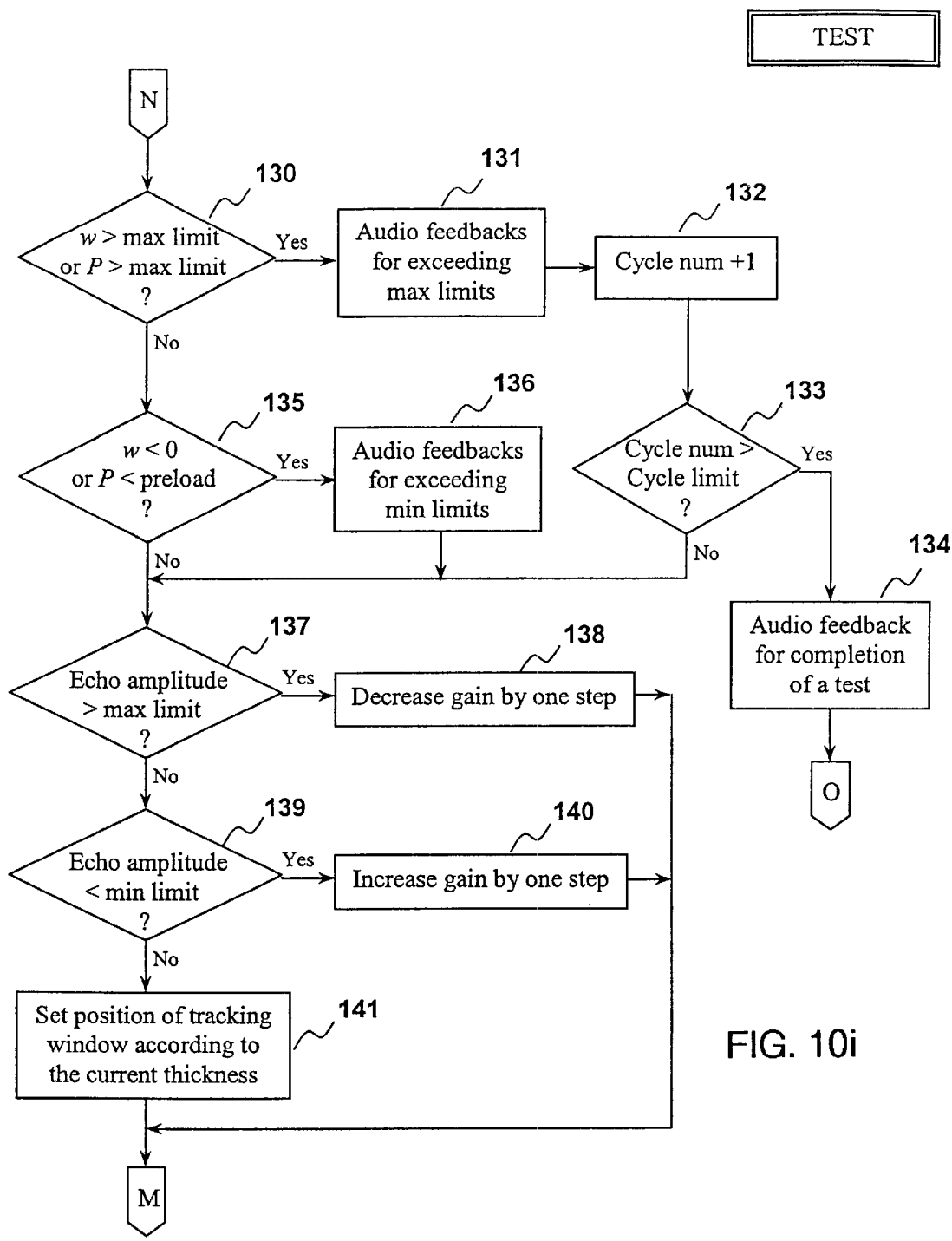

The flowchart of the subprogram PRETEST is illustrated in FIGS. 10*e* and 10*f*. The subprogram PRETEST first prompts pretest status on the LCD (block 89). Then the width of the track window is set large enough to cover the valid tissue depth, for example 15 cm (block 90). The leading edge of the track window is set just after the falling edge of the transmitting pulse to avoid its influence. The gain of the ultrasound receiver is set to be maximal (block 91). After these parameters have been set, the subprogram MEASUREMENT is used (block 92) to make a measurement of load and thickness.

Figure 10J:
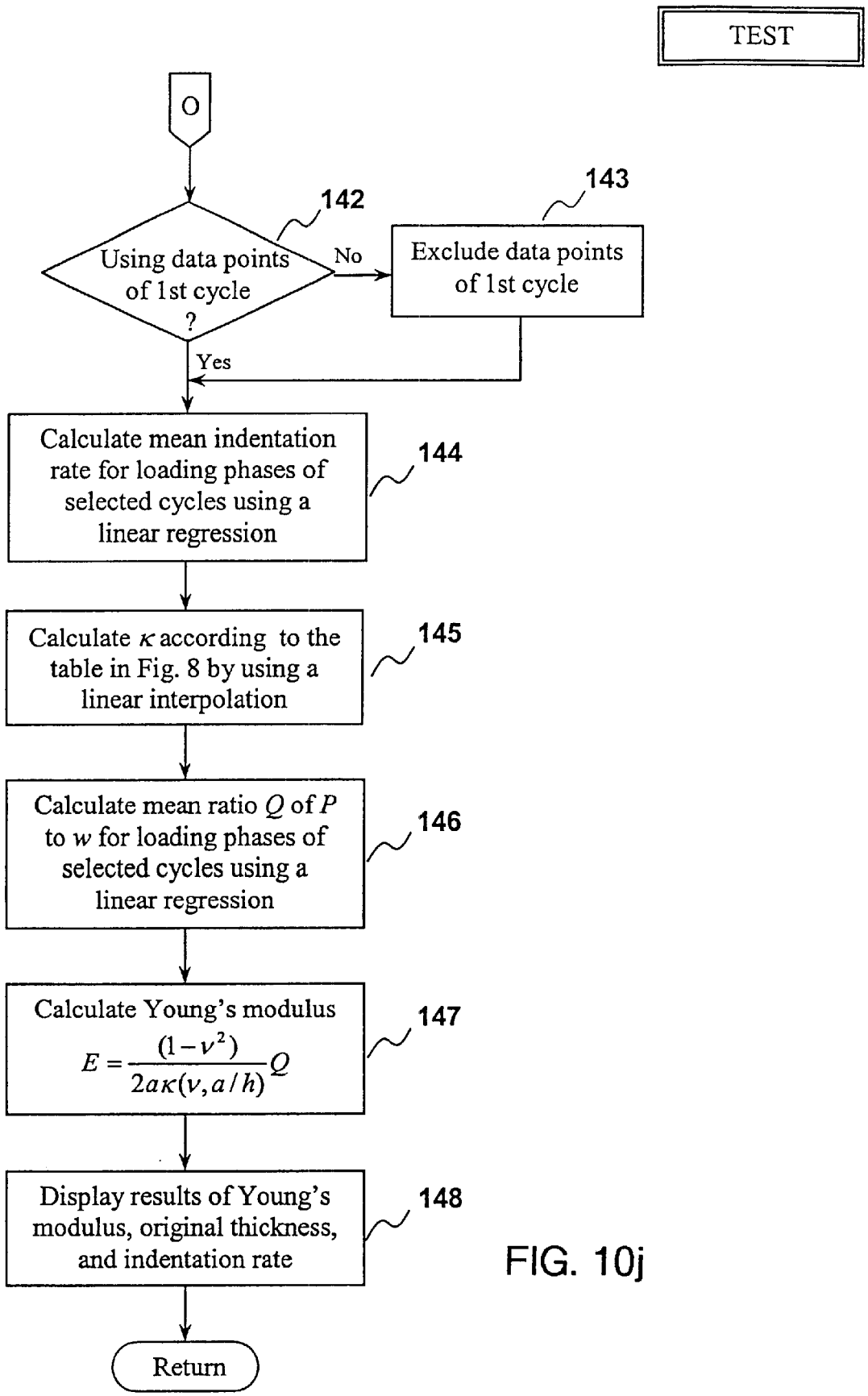
Figure 10K:
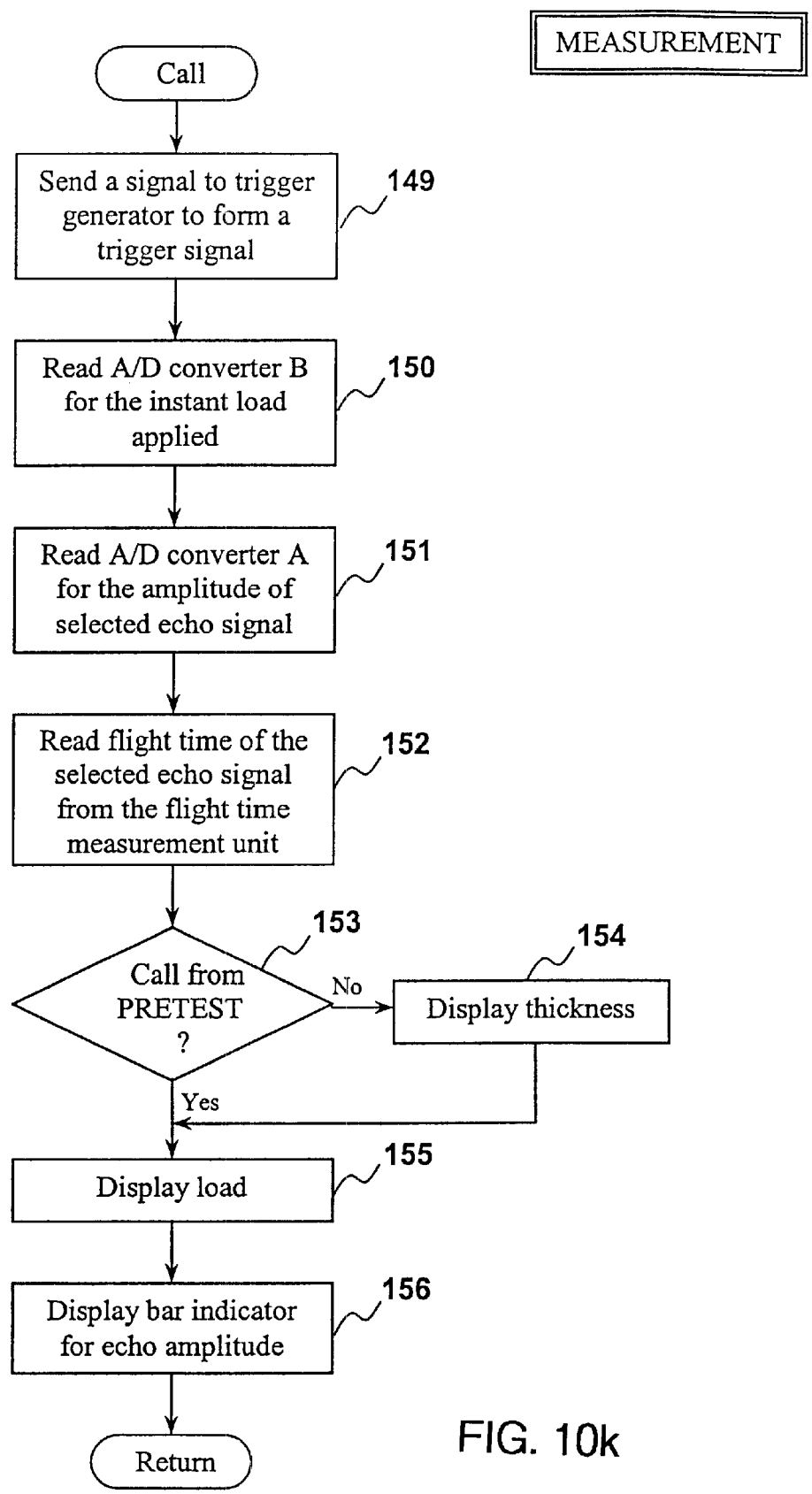

The flowchart of the subprogram MEASUREMENT is illustrated in FIG. 10*k*. The subprogram MEASUREMENT first sends a signal from microprocessor 26 via I/O ports to the trigger generator 35 to form a trigger signal 37 (block 149). Then the digitized load data is read from the A/D converter B 34 (block 150), and the digitized peak amplitude of the echo within the track window 43 is read from the A/D converter A 33 (block 151). The flight time of the selected echo signal is read from the flight time measurement unit (block 152).

Figure 11:
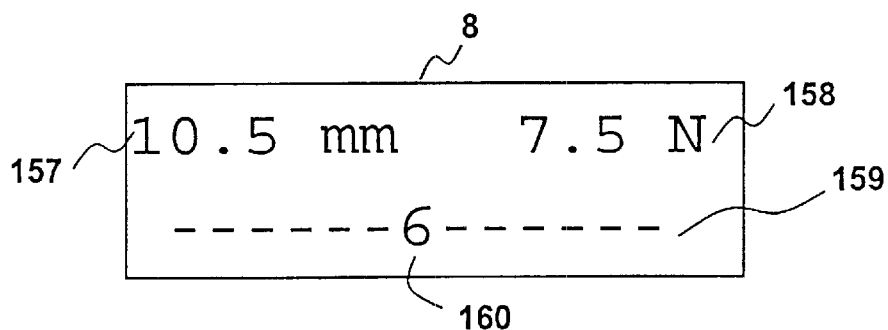
FIG. 11 is a display showing in real time tissue thickness and load data, and a bar indicator for the relative amplitude of the ultrasound reflection signal during a cyclic test.

FIG. 11 shows a display in real time of the tissue thickness and the load as the subprogram MEASUREMENT. For the subprogram PRETEST (block 153), the thickness is not displayed. otherwise, the instant thickness (157) is displayed on the LCD 8 (block 154). The instant load (158) is displayed on the LCD 8 in both cases (block 155) In addition, a bar indicator 159 with levels of, for example, eight, is displayed on the LCD (block 156) to show the relative amplitude of the echo peak. The figure (O to 7) in the middle (160) equals the number of bars.

Thereafter the program returns from the subprogram MEASUREMENT (block 92) and first checks if the operator attempts to reset the load offset or not (block 93). If the keypad for the load offset reset is pressed, the current load reading is set to be the zero offset of load (block 94). Then, the program checks the amplitude of the echo peak. If the amplitude is larger than a preset maximum limit (block 95), the gain of the ultrasound receiver is reduced for one step (block 96), for example, 1 dB. Similarly, if the amplitude is smaller than a preset maximum limit (block 97), the gain is increased for one step (block 98), for example, 1 dB. The maximum and minimum limits of echo amplitude are preset in the program, for example, for an 8 levels (0–7) range of relative amplitude, the minimum limit can set to 3, and the maximum limit can be set to 6. Finally, the program checks if the operator attempts to start a pretest (block 99). If the starting key is pressed, a pretest will be performed. Otherwise, the subprogram MEASUREMENT is called up again, and the above steps are repeated. Repetition can be very fast, for example, 50 times in one second, and the echo amplitude can be adjusted quickly to an accepted level, i.e., larger than the minimum limit and smaller than the maximum limit. The operator is responsible to align the probe 1 as perpendicularly as possible to the underlying bony interface by monitoring the indicator 159 and 160 for echo amplitude on the LCD panel 8 and maintaining the amplitude level as large as possible. When an accepted level of echo amplitude is presented by the amplitude indicator 159 and 160 and an expected pre-load is shown on the LCD panel 8, the operator can start to search the tissue thickness by pressing the starting key.

When the starting key is pressed, the program first sets a small track window with a width of, for example, 2 $\mu$s (block 100). The leading edge of the track window is set just after the falling edge of the transmitting pulse. By moving this small window, the program searches for valid thicknesses (block 101 through 107). If a valid thickness is determined, it means that there is a valid echo signal at the depth equal to that thickness. The number of valid thicknesses is set to zero before the searching procedure (block 101). By calling up the subprogram MEASUREMENT, the instant load and thickness are measured (block 102). If the measured thickness is smaller than a preset maximum limit, for example, 15 cm, it is assumed to be a valid thickness and is recorded with the corresponding load, and the number of valid thickness is increased by 1 (blocks 103, 104, 105) Otherwise, the measured thickness is not a valid thickness, and it means that there is no echo within the track window, or the amplitude of echo is too small to detect. The window position is then increased by one step of, for example, 2 µs, to search for a larger thickness (block 106). If the window position does not exceed the maximum position limit (block 107), then the subprogram MEASUREMENT is called up again and the above steps (block 102 though 107) are looped. Otherwise, the program skipped from the loop, and the number of valid thicknesses is checked (block 108). If the number of valid thicknesses is zero, i.e., there is no valid echo, then an error flag is set and an error message is prompted on the LCD panel 8 (block 109). Otherwise, there is at least one valid echo detected, and the number of valid thickness is larger than zero. The largest thickness is displayed and assumed to be the real thickness from the tissue surface to the bony interface (block 110). The corresponding load is also displayed and assumed to be the pre-load (block 110). Finally, an audio feedback is given to indicate the completion of a pretest (block 111), and the program returns to where the subprogram PRETEST is called (block 52).

After the pretest, the operator can select to start a cyclic test, to change the tissue thickness and the pre-load based on the results of pretest, to change other parameters, or to perform pretest again (block 70 through 76), as shown in FIG. 10c. If the load applied during pretest is a little different from the pre-load expected, the operator can select to adjust the pre-load for the cyclic test (block 70, 71). If multi echoes are detected, and more than one thickness is determined, the operator can select other thickness rather than the maximum one assumed by the program to be the real tissue thickness (blocks 72, 73, 74), This operation is needed only for the soft tissue with a rather flat tissue-bone interface where multi-reflections of an ultrasound echo will normally occur. If the operator selects to perform a pretest again (block 75), the program skips to the step of pretest (block 52). If the operator selects to change other parameters (block 76), the program skips to the step of changing parameters (block 58).

If the starting key is pressed after a pretest (block 53), the test number is set to zero, the subprogram TEST is then called (block 54), and a cyclic test can be performed. The flowchart of the subprogram TEST is illustrated in FIGS. 10g–j. First, the gain of the ultrasound receiver is set to the same value as that used in the pretest (block 112), and a small track window with a width of, for example, 2 µs, is set with the central position located at the rising edge of the select echo, from which the tissue thickness is determined in the pretest (block 113).

Then, the subprogram MEASUREMENT is called to make a measurement of the load and the tissue thickness (block 114). After the measurement, the echo amplitude is checked and the gain is adjusted accordingly (block 115 through 118). The operation is the same as that described in the subprogram PRETEST (block 95 through 98). If the gain exceeds the maximum limit and the determined thickness is larger than the maximum thickness limit (block 119), for example, 15 cm, the program prompts an error message to show that no valid echo is detected within the track window (block 120). After these steps, the subprogram MEASUREMENT is called again (block 114). As stated in the description for the subprogram PRETEST, the above steps are looped quickly, and the gain is automatically adjusted to a proper level to make the echo amplitude an acceptable value. The operator can align the probe properly to obtain a valid echo from the tissue-bone interface for measurement by monitoring the amplitude bar indicator 159 and 160. When the operator is satisfied with the echo amplitude and the pre-load applied, a cyclic measurement can be started by pressing the starting key (block 121).

The tissue thickness measured just before the starting key pressed is assumed to be the initial thickness of soft tissue (block 122). The data number and the cycle number are set to be zero (block 123), and the subprogram MEASUREMENT is called (block 124). If the gain exceeds the maximum gain limit, and the determined tissue thickness is larger than maximum thickness limit (block 125), for example, 15 cm, the program sets an error flag, prompts an error message to show that no valid echo is detected within the track window (block 126), and returns to where the subprogram is called (block 54). Otherwise, the indentation depth w is calculated by subtracting the initial tissue thickness from the current measured thickness (block 127). The indentation depth w and applied load P are recorded in the data points array (block 128), and the data number is increased by one (block 129). If the indentation depth w or the load P exceeds the maximum limits or minimum limits, audio feedbacks are provided (blocks 130, 131, 135, 136). The audio feedbacks can be, for example, two different tones from the buzzer, to indicate exceeding maximum and minimum limits, respectively. The operator can load and unload the probe 1 on the tissue surface to perform cyclic tests according to the audio feedbacks. Thus, the pre-load, maximum load and maximum indentation depth are manually controllable. After these steps, the gain is adjusted according to the echo amplitude (block 137 through 140), and the position of the track window is adjusted according to the current thickness measured to make the middle of the window at the same position of the rising edge of the selected echo (block 141). Then the subprogram MEASUREMENT is called again (block 124), and the above steps are looped (block 124 through 141). On the other hand, after every exceeding of the maximum limit is detected, the cycle number is increased by one (block 132). If the cycle number exceeds the cycle limit (block 133), an audio feedback, which differs from those for the load or indentation depth exceeding maximum and minimum limits, is provided to indicate the completion of a cyclic test (block 134).

After collecting the data points for a cyclic test, the Young's modulus and the indentation rate are calculated and the results are displayed on the LCD 8 (block 142 through 148). The flowchart of these steps is shown in FIG. 10j.

Figure 5:
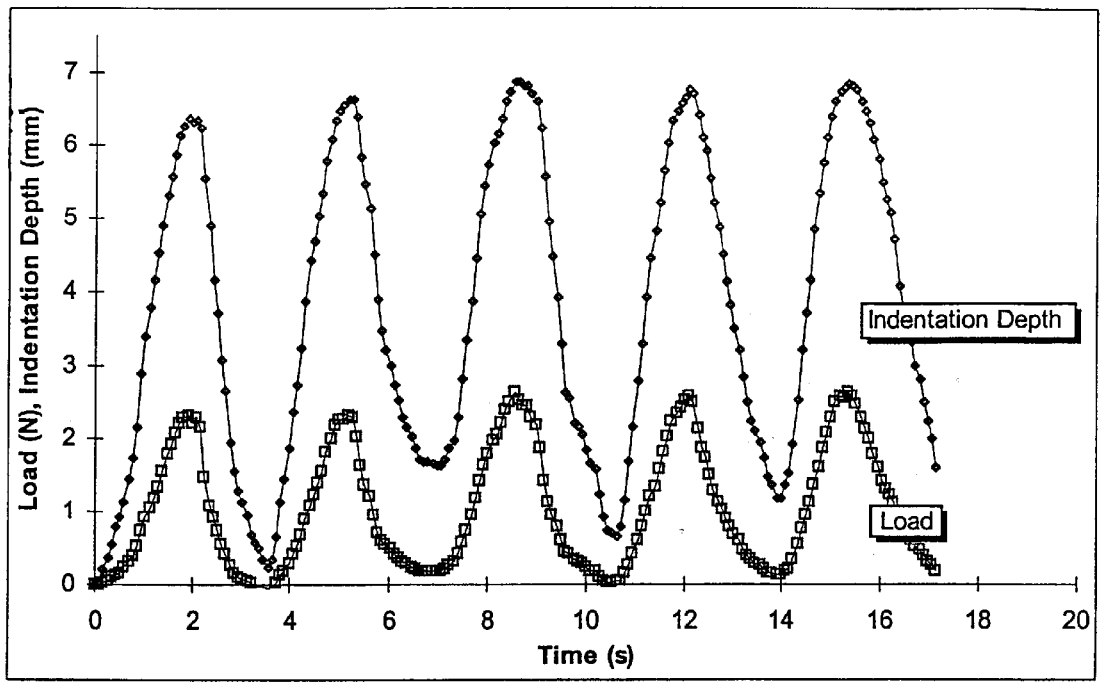
FIG. 5 are load and indentation sequences of a cyclic test determined by the device.
Figure 6:
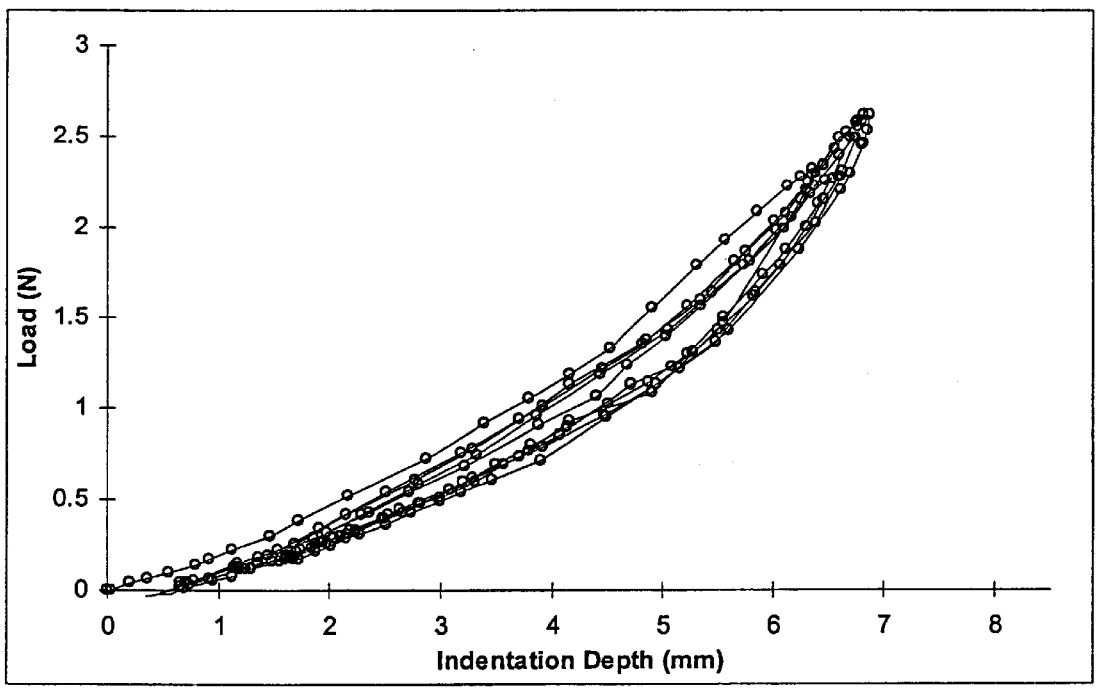
FIG. 6 is a load-indentation curve plotted in accordance with FIG. 5.
Figures 7, 8:
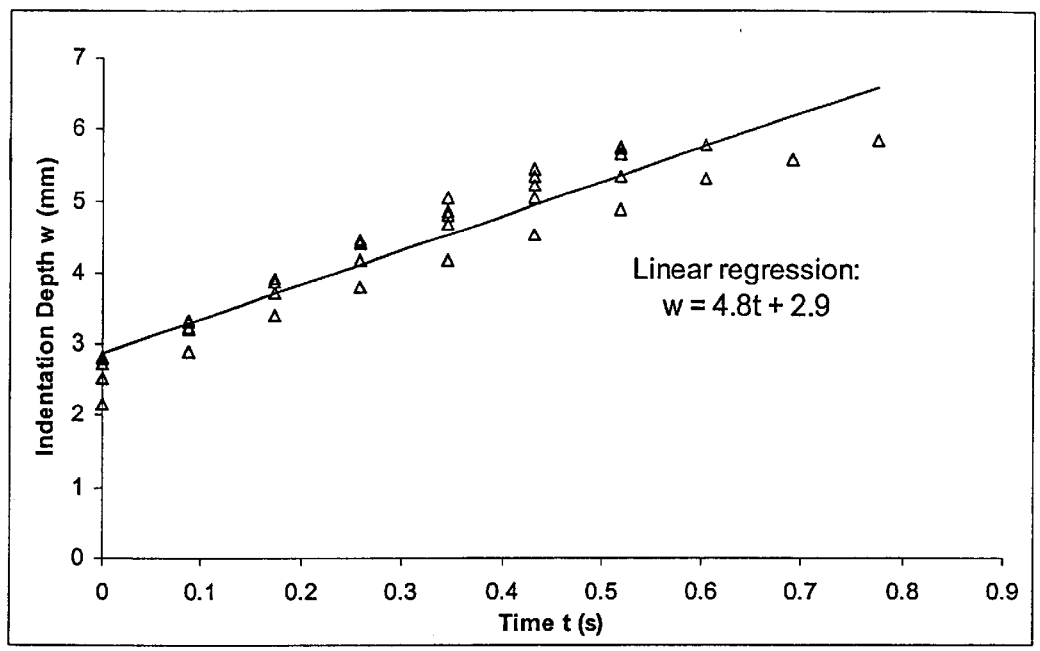
FIG. 7 illustrates a graph for use in calculating a mean indentation rate using a linear regression. (Data points of the loading phases with load≧preload (0.5 N) and ≦maximum load (2.5 N), and indentation ≧0 and ≦maximum indentation (30%) are included from data of FIG. 5 and FIG. 6.)
FIG. 8 is a table showing the dependence of a scaling factor K to an aspect ratio a/h and Poisson's ratio v. (From W. C. Hayes et al, *A mathematical analysis for indentation tests of articular cartilage*, Journal of Biomechanics; Vol. 5, 541–551 (1972))

FIG. 5 shows an example of load and indentation sequences of a cyclic test, and FIG. 6 is the load-indentation curve plotted in accordance with FIG. 5. In the calculation, the data points of the first cycle are excluded (block 142, 143) if it is selected to do so (block 60, 61) The operator may not control the loading and unloading sequence well during the first cycle of a cyclic test, So exclusion of the first cycle improves the validity of the results. The mean indentation rate for the loading phases of the selected cycles is then calculated using a linear regression as shown in FIG. 7 (block 144). The first data point of each selected cycle is re-scaled to zero in time, and the time scales of other data points are adjusted accordingly. The Linear regression is operated for these re-scaled data points. The slope of the regression line is defined as the mean indentation rate. In the example shown in FIG. 7, the mean indentation rate is 4.8 mm/s.

Figure 9:
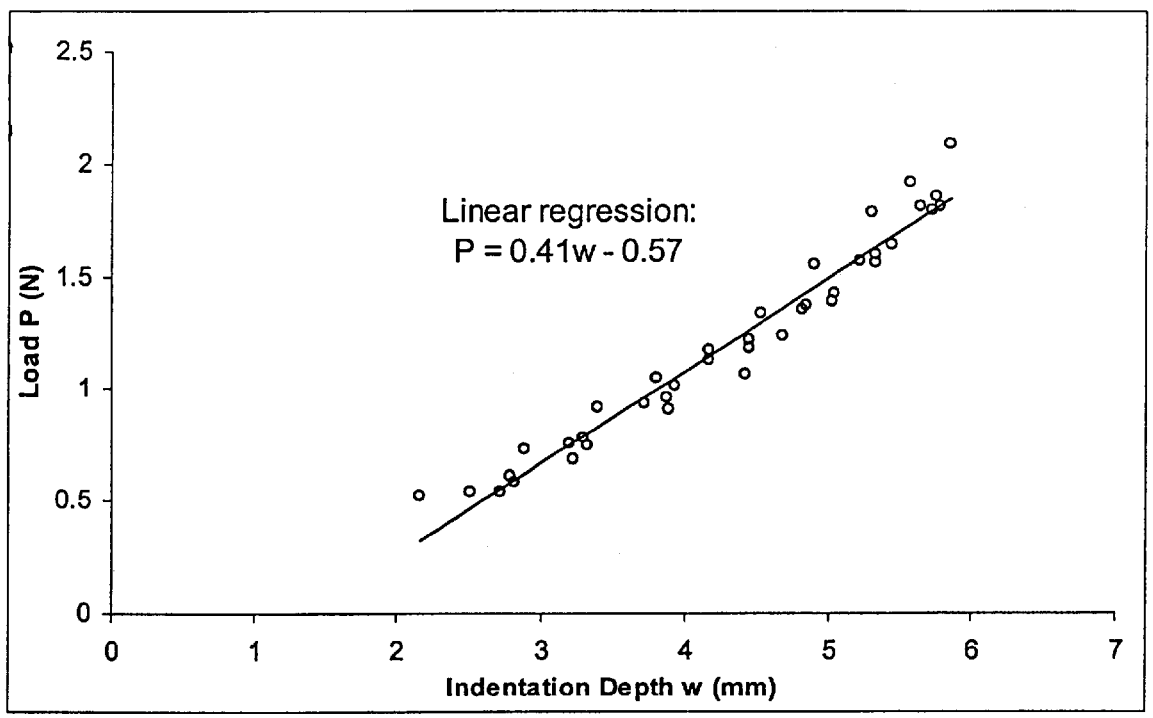
FIG. 9 is a graph for use in calculating a mean ratio of load P against indentation depth w. (Data points of loading phases with load≧preload (0.5 N) and ≦maximum load (2.5 N), and indentation≧0 and ≦maximum indentation (30%) are included from data of FIG. 5 and FIG. 6)

For the calculation of Young's modulus using the indentation model as shown in Equation (1), the scaling factor K is calculated from the table as shown in FIG. 8 using a linear interpolation (block 145). The Possion's ratio v is assumed to be 0.45 for soft tissues. In this embodiment, the indentor radius a is 4.5 mm, and the calculated original tissue thickness is 19.6 mm. With these parameters, the scaling factor is calculated to be 1.3. The mean ratio Q of the load P to the indentation depth w for the loading phases of the selected cycles calculated using a linear regression is shown in FIG. 9 (block 146). In this example shown in this figure, the mean ratio Q is 0.28 N/mm. Derived from Equation (1), the Young's modulus of the soft tissue is calculated using equation (2) (block 147):

$$E = \frac{(1-v^2)}{2aK(v, a/h)} Q \qquad (2)$$

For this example, the calculated Young's modulus is 19 kPa. After the calculation, the results of this cyclic test are automatically displayed on the LCD panel 8 (block 148), and the program returns to where it is called (block 54).

Figure 12:
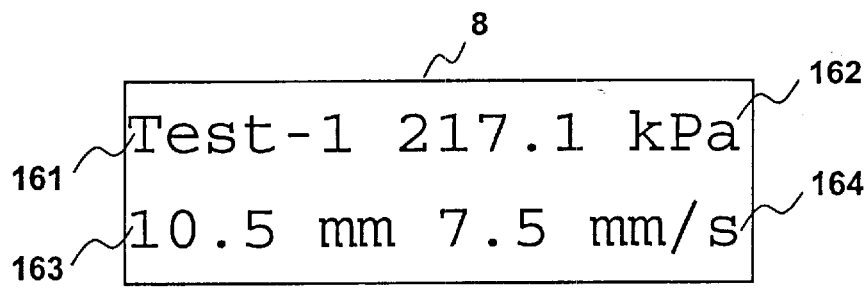
FIG. 12 is a display showing a determined Young's modulus, the original tissue thickness and the indentation rate after a cyclic test is completed.

FIG. 12 is a display showing the number of cyclic test (161), the Young's modulus (162), the original thickness (163), and the mean indentation rate (164).

As shown in FIG. 10*d*, after a cyclic test, the operator can select to perform another cyclic test (block 55), to show results of another test if more than one test have been performed (block 78, 79), to show the average (AVG) and the standard deviation (SD) of the results of all tests (block 80, 81), to delete results of a test (block 82, 83), to erase results of all tests and start a new group of tests (block 84, 85), to perform pretest again (block 86), or to change parameters (block 87).

Figure 13A:
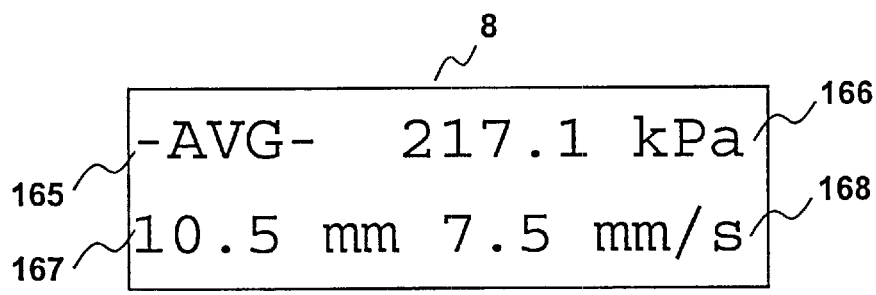
FIGS. 13a and 13b are displays showing the mean and the standard deviation of the Young's modulus, the original tissue thickness and the indentation rate after a group of cyclic tests are completed.
Figure 13B:
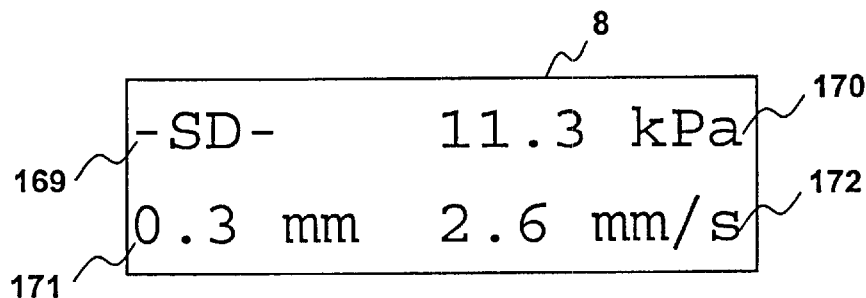

FIGS. 13*a* and 13*b* are displays of showing the average (165) and the standard deviation (169) of the Young's modulus (166, 170), the original tissue thickness (167, 171), and the indentation rate (168, 172) of a group of cyclic tests.

If performing another test is selected (block 55) and the number of cyclic tests is not larger than the maximum limit (block 56), the test number is increased by one (block 57). The subprogram TEST is called again (block 54), and another cyclic test can be performed. The above steps are looped until enough cyclic tests are conducted, other options are selected, or the program is interrupted by the operator.

We claim:

1. A portable ultrasonic palpation device comprising a hand held probe for palpation measurements including, arranged in series, mechanically, from an application tip of the probe for application to an outer surface of a soft tissue layer of which Young's modulus is to be measured, an ultrasonic transducer for launching and detecting ultrasound at the outer surface of the tissue layer and a pressure sensor for detecting the pressure applied to the tissue layer through the probe.

2. The portable ultrasonic palpation device according to claim 1, wherein the probe comprises a first cylindrical body having a forward tip, including the application tip, containing the ultrasonic transducer, and a second cylindrical body attached end-to-end to the first cylindrical body and containing the pressure sensor.

3. The portable ultrasonic palpation device according to claim 2, wherein the first and second cylindrical bodies have respective diameters of approximately 10 mm.

4. A portable ultrasonic palpation device comprising:

a hand held probe for palpation measurements including, arranged in series, mechanically, from an application tip of the probe for application to an outer surface of a soft tissue layer of which Young's modulus is to be measured, an ultrasonic transducer for launching and detecting ultrasound at the outer surface of the tissue layer and a pressure sensor for detecting the pressure applied to the tissue layer through the probe; and a computer connected to receive signals from the transducer and from the pressure sensor and programmed to compute the Young's modulus of the tissue layer based on the signals received.

5. The portable ultrasonic palpation device according to claim 4, wherein the computer is programmed to determine depth of the tissue layer from the outer surface to an underlying structure harder than the tissue layer.

6. The portable ultrasonic palpation device according to claim 4, wherein the computer is programmed to compute $$\frac{E(1-v^2)P}{2aK(v, a/h)w}$$

where

E is the Young's modulus, v is Poisson's ratio,

P is pressure applied through the probe, w is indentation depth in the tissue layer, h is thickness of the tissue layer, a is radius of an indentor of the probe, and K is a scaling factor.

* * * * *